United States Patent [19]

Willock et al.

[11] 4,063,554
[45] Dec. 20, 1977

[54] SINGLE NEEDLE ALTERNATING FLOW BLOOD PUMP SYSTEM

[76] Inventors: Charles B. Willock, 16222 SE. Oatfield Road, Milwaukie, Oreg. 97222; Roger E. Wood, 1601 Jefferson St., Oregon City, Oreg. 97045

[21] Appl. No.: 677,722

[22] Filed: Apr. 16, 1976

Related U.S. Application Data

[63] Continuation of Ser. No. 521,502, Nov. 6, 1976, abandoned.

[51] Int. Cl.² .............................................. A61M 1/03
[52] U.S. Cl. ............................ 128/214 R; 128/214 F; 210/89
[58] Field of Search ........... 128/214 R, 214 B, 214 E, 128/214 F, 214.2, DIG. 3; 210/89, 321 B

[56] References Cited

U.S. PATENT DOCUMENTS

| 3,756,234 | 9/1973 | Kopp | 128/214 R |
| 3,791,767 | 2/1974 | Shill | 128/DIG. 3 |
| 3,830,234 | 8/1974 | Kopp | 128/214 R |
| 3,848,592 | 11/1974 | Willock | 128/214 R |

OTHER PUBLICATIONS

Twiss; Lancet, Nov. 21, 1964; p. 1106 (No. 7369).

*Primary Examiner*—Dalton L. Truluck
*Attorney, Agent, or Firm*—Klarquist, Sparkman, Campbell, Leigh, Hall & Whinston

[57] ABSTRACT

A blood pump system, typically employed in dialysis, includes a blood pump for withdrawing blood via a single hypodermic needle and valve means operated in a synchronism therewith for returning treated blood via the same hypodermic needle. The operation of the blood pump is cyclically interrupted and the valve means opened for the alternate withdrawal and return of blood.

8 Claims, 3 Drawing Figures

SINGLE NEEDLE ALTERNATING FLOW BLOOD PUMP SYSTEM

CROSS REFERENCE TO RELATED APPLICATION

This application is a continuation of copending application Ser. No. 521,502, filed Nov. 6, 1976, now abandoned.

BACKGROUND OF THE INVENTION

This invention relates to a single needle blood pump system, and particularly to such a system wherein blood flow and pressure are easily regulated.

In the use of an "artificial kidney", dialysis of the patient's blood requires some means of withdrawing the blood from the patient's body and returning the same after treatment. With cannulae, providing permanent tubular connection to the patient, connection of the patient to the dialyzer apparatus is facilitated. However, a patient may not tolerate this arrangement because of infection or the like. Alternatively, plural hypodermic needles may be inserted in a patient's vein after insertion of a fistula between a vein and artery, with one needle being utilized for withdrawal of blood while a second needle is employed to return blood to the vein. A more desirable system would avoid the requirement for repeated insertion of both needles.

A prior art single needle system withdraws and returns blood via the same hypodermic needle and includes a pair of clamp valves employed in two connections to the hypodermic needle so that blood can be alternately withdrawn and returned therethrough. In this system the valves are solenoid operated in response to pressure detected at a dialyzer output. However, pumping in such a system tends to produce a vacuum at the pump inlet, flattening the plastic tubing and causing cessation of system operation.

According to copending application Ser. No. 348,509 entitled "Single Needle Alternating Flow Blood Pump System" filed Apr. 6, 1973, by Charles B. Willock, incorporated herein by reference, a single needle system comprises a blood flow loop including a blood pump and valve means operated by the blood pump for returning blood to the patient when the pump is periodically turned off. This system has the advantage of simplicity, reliability and absence of dependence upon detected pressure. Moreover, the periodically operating pump does not cause flattening of the plastic tubing in the blood flow loop.

SUMMARY OF THE INVENTION

According to the present invention, a liquid flow loop is connected at either end to a single path such as a hypodermic needle. This loop includes a blood pump for transporting liquid in the loop, and valve means for temporarily impeding the passage of liquid. The blood pump and the valve means operate synchronously for the alternate pumping and opening of the valve means, whereby liquid is alternately withdrawn and returned via the single path. A timer is coupled in control relation to the blood pump for regularly energizing the same to pump liquid during first intervals separated by second non-pumping intervals. The timer is further coupled in control relation to the valve means for regularly operating said valve means in substantial synchronism with the blood pump for alternate withdrawal and return of blood via the same needle. In this system, the flow of blood is independently adjustable by adjusting the speed of operation of the blood pump, and control of blood pressure is facilitated.

It is accordingly an object of the present invention to provide an improved alternating flow blood pump system for alternate removal of blood from a blood vessel and return to said blood vessel via a single needle.

It is a further object of the present invention to provide an improved single needle alternating flow blood pump system which is reliable in operation, and economical in construction.

It is a further object of the present invention to provide an improved and simplified single needle alternating flow blood pump system having an increased number of control parameters.

It is a further object of the present invention to provide an improved single needle alternating flow blood pump system wherein the total blood flow is adjustable independently of the alternating flow cycle.

It is a further object of the present invention to provide an improved single needle alternating flow blood pump system wherein blood pressure is more readily controllable.

The subject matter which we regard as our invention is particularly pointed out and distinctly claimed in the concluding portion of this specification. The invention, however, both as to organization and method of operation together with further advantages and objects thereof, may best be understood by reference to the following description taken in connection with the accompanying drawings wherein like reference characters refer to like elements.

DRAWINGS

DETAILED DESCRIPTION

Figure 1:
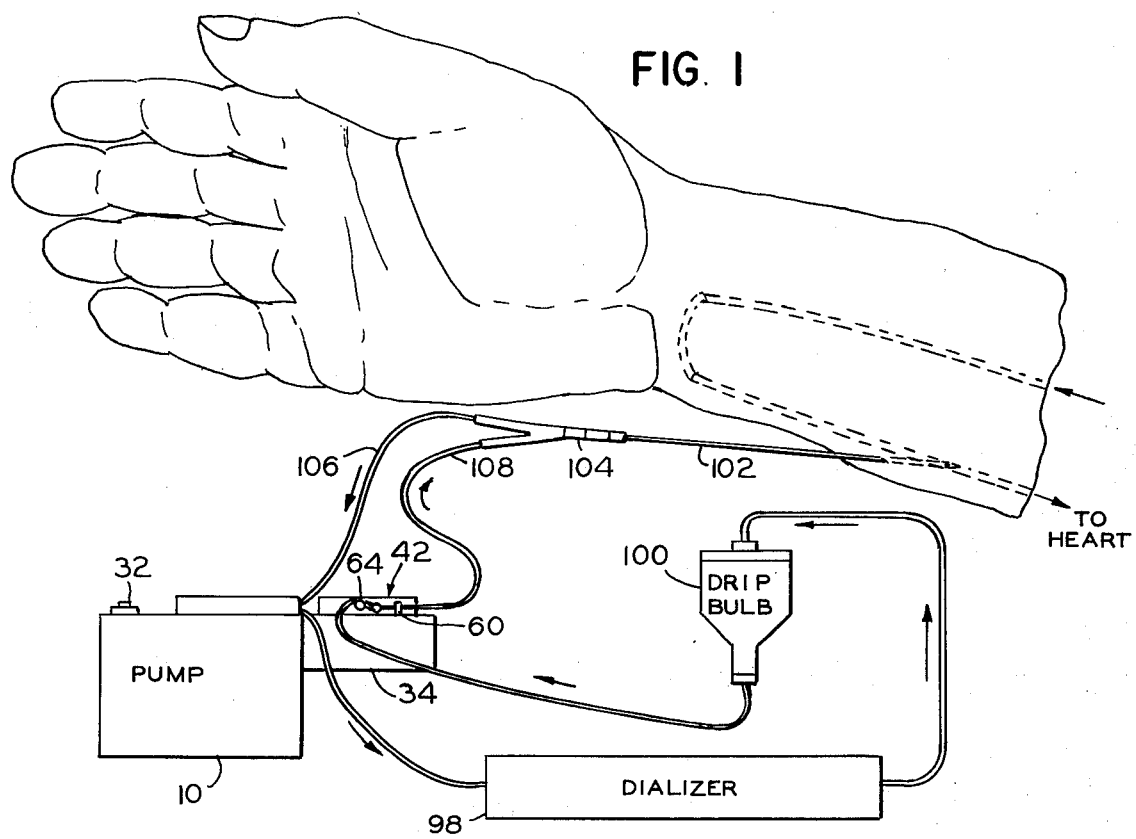
FIG. 1 is an overall view of a single needle alternating flow blood pump system.

A single needle blood pump system as set forth in the aforementioned application Ser. No. 348,509 is illustrated in FIG. 1 wherein a blood flow path or loop includes blood pump 10, a blood receiving or treatment means typically comprising a dialyzer 98, a drip bulb 100, and a valve or clamp comprising pump operated arm 42 and clamping pin 60 between which tubing section 64 is received. A blood flow loop comprising a blood set alternately withdraws blood from a single path comprising a hypodermic needle 102, drawing the blood through the blood pump and into the dialyzer, and then expelling blood into the hypodermic needle as the valve 42, 60 opens. Common connection with both ends of the blood flow loop and the hypodermic needle is made by Y connection means 104.

The blood pump 10 is a conventional roller-and-flexible-tube type, including a rotatable rotor carrying a pair of diametrically spaced rollers. As the rotor is rotated, the rollers engage a segment of tubing 106 disposed in a semi-circle and the pump thereby provides positive displacement by forcing liquid along the tubing in the direction of the arrows in the drawing. The speed of rotor rotation is suitably controlled by an adjusting knob 32. One of the rollers on the pump rotor contacts arm 42 each time the rotor rotates through 180°. On each such occasion, action of the pump is temporarily suspended and valve 42, 60 opens as arm 42 moves or rotates away from pin 60. This action is further described in the aforementioned prior application Ser. No. 348,509.

The blood receiving means 98 comprising a dialyzer or the like is capable of receiving pressure as the membrane thereof expands slightly such that blood is forced into the hypodermic needle when valve 42, 60 opens. Thus, blood is drawn from the hypodermic needle through tubing portion 106 and delivered to the dialyzer as the pump rotor rotates through 180°. At this time, the pump rotor stops since arm 42 actuates a limit switch 70 (in FIG. 2) while valve or clamp 42, 60 opens returning blood to the hypodermic needle via tubing portion 108. At such time, the blood pump rollers themselves prevent the flow of blood through tubing portion 106 in the direction of the pump, i.e., the pump acts as the clamp or valve. After a predetermined time, governed according to timer 76a in FIG. 2, the pump resumes rotation and valve 42, 60 is re-closed so that blood is once again withdrawn from the hypodermic needle. In a typical instance, the timing of timer 76a and the speed of rotation of the blood pump are adjusted so that the time of rotation of the pump rotor through 180° is approximately one-half second, and the temporary interruption in blood pump operation is also approximately one-half second.

Figure 2:
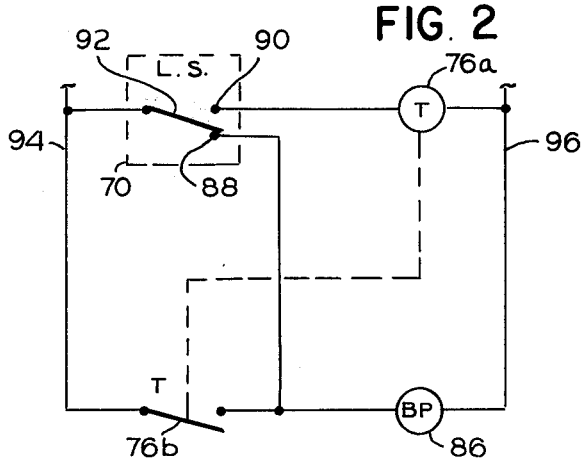
FIG. 2 is a diagram illustrating an electrical control circuit employed with the FIG. 1 system.

FIG. 2 is an electrical circuit diagram illustrating the connection of limit switch 70 operated by arm 42, timer 76a and blood pump motor 86. Limit switch 70 has a normally closed contact 88 and a normally open contact 90, these contacts providing the indicated connection until the limit switch is operated by movement of arm 42, whereupon the movable contact 92 opens a circuit from power line 94 to contact 88 and closes a circuit from power line 94 to contact 90. One side of blood pump motor 86 is connected to power line 96, and until actuation of the limit switch a circuit from the blood pump motor is also completed to power line 94 through contacts 92 and 88 bringing about motor operation and rotation of rotor 12. However, when the blood pump rotor moves to a position whereby arm 42 is rotated, the limit switch 70 disconnects motor 86 whereby blood pump rotor rotation is temporarily halted. At the same time, timer 76a is energized via limit switch contact 90, and at the conclusion of a preset time period timer 76a closes normally open contacts 76b for re-energizing blood pump motor 86, the circuit being completed from power line 94 through contacts 76b and the blood pump motor to power line 96. Thereupon, the blood pump rotor resumes rotation and the limit switch contacts resume their position illustrated in the drawing whereby blood pump motor 86 remains energized after the timer contacts reopen. The blood pump rotor will then continue rotation until the next roller thereof engages arm 42, i.e., 180° later.

The hypodermic needle 102 may be inserted in an arm vein of a patient provided with a fistula by operative procedure, the latter causing expansion of the vein and allowing easier insertion of the hypodermic needle. The hypodermic needle, which may comprise a 14-gauge needle, is inserted in the direction of blood flow. Typically, the patient must undergo periodic dialysis and thus must reinsert the hypodermic needle at frequent intervals. The present system permits the insertion of only one hypodermic needle, rather than two as in the case of the more conventional procedure, and is of appreciable advantage from the patient's point of view. The present system can also effect 200 cc per minute transfer of blood. The present system, wherein blood is alternately withdrawn from the vein of the patient and returned through a single hypodermic needle, and wherein such withdrawal and return are synchronized primarily according to the operation of the blood pump, is preferable to a system wherein a pump is continuously operated since in the latter instance undesired vacuum then produced on the input side of the pump may cause tube flattening or the like. Moreover, the present system does not require pressure gauge control therefor but advantageously functions in response to the cyclical operation of the blood pump itself or in synchronism therewith.

Figure 3:
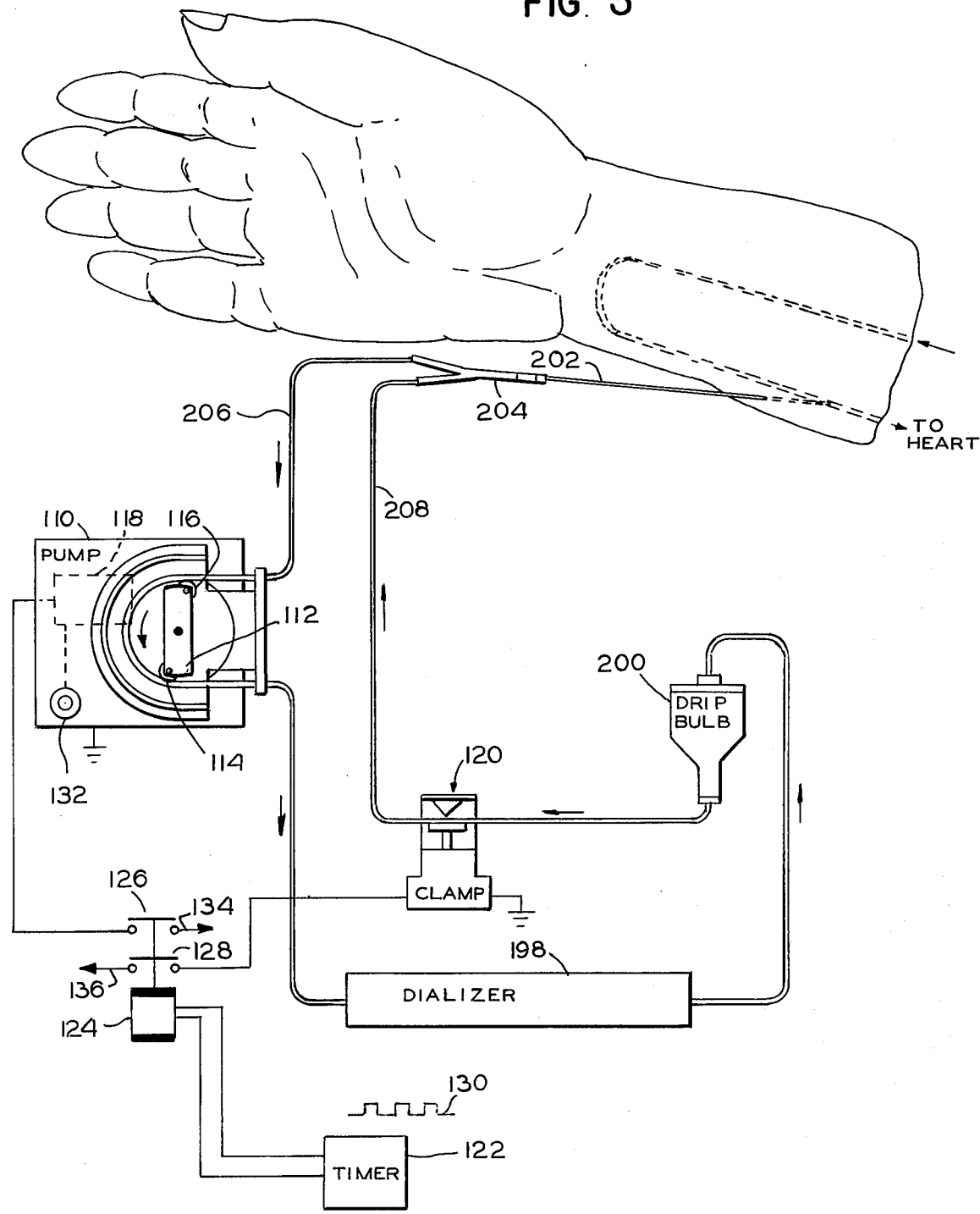
FIG. 3 is a view of a single needle alternating flow blood pump system according to the present invention.

Referring to FIG. 3, a system according to the present invention is illustrated for providing enhanced adjustability relative to the flow of blood and the blood pressure. A blood flow path or loop includes blood pump 110, a blood receiving or treatment means typically comprising a dialyzer 198, a drip bulb 200, and a solenoid operated valve or clamp 120 adapted to close off the flow of blood in tubing portion 208 when the solenoid is energized. It is noted the clamp is separate from pump 110. A blood flow loop comprising a blood set ultimately withdraws blood from a single path comprising hypodermic needle 202, drawing the blood through the blood pump and into the dialyzer, and then expelling blood into the hypodermic needle when the valve 120 is opened. Common connection with both ends of the blood flow loop and the hypodermic needle is made by Y connection means 204.

Blood pump 110 is a roller-and-flexible-tube type pump, including a rotor 112 rotated by DC motor 118, the rotor carrying a pair of diametrically spaced rollers 114 and 116. As the rotor is rotated, the rollers 114 and 116 engage a segment of tubing 206 disposed in a semicircle around the inside of a U-shaped guide. The pump thus provides positive displacement, forcing liquid along the tubing in the direction of the arrows in the drawing. The speed of rotor rotation is controlled by adjusting knob 132 which is coupled in a conventional manner for adjusting the speed of DC motor 118. Blood receiving means 198 comprises a dialyzer or the like and is capable of receiving pressure. Blood is forced into the hypodermic needle when valve 120 is open.

According to the present invention, blood pump 110 and solenoid clamp 120 are operated in substantial synchronism on a substantially periodic basis by means of timer 122 which controls relay coil 124 for regularly closing energizing contacts 126 and 128, respectively connected to blood pump motor 118 and the solenoid of clamp 120. Thus, when contacts 126 are closed, a circuit is completed from blood pump motor 118 to a source of DC power via lead 134 whereby motor 118 causes rotor 112 to rotate at a speed determined by control 132. Furthermore, when coil 124 is energized, contacts 128 are closed and a circuit is completed from the solenoid of clamp 120 to a source of power via lead 136, and clamp 120 is actuated for clamping tubing portion 208 to prevent the flow of blood therealong.

Timer 122 is suitably a Potter & Brumfield timer Model CRB-48-70010, and its operation is described by waveform 130 illustrating the energizing voltage supplied to coil 124, wherein the positive going portions of the cycle indicate energization of said coil. The timer suitably operates according to a time constant of a resistor-capacitor combination, with the timing and the duty cycle of the timer being adjustable by means not shown.

According to the present system, the on and off periods are comparable but preferably the off periods between energization times of coil 124 are slightly longer than the energization periods. The timer waveform is desirably periodic and thereby brings about operation of blood pump 110 and clamp 120 on a periodic basis whereby pump 110 is energized during first intervals, i.e. when contacts 126 are closed, separated by second non-pumping intervals when contacts 126 are open. During the non-pumping intervals, the blood pump rollers 114 and 116 themselves prevent the flow of blood through tubing portion 206 in the direction of the pump.

During the said first intervals when the pump is causing the transfer of blood along the blood flow loop towards receiving means 198, clamp 120 is also operated to close tubing portion 203 whereby pressure builds up in dialyzer 198, drip bulb 200, and the connecting tubing. During second or nonpumping intervals when coil 124 is deenergized, the clamp opens and blood returns to the hypodermic needle via tubing portion 208 under the pressure built up during the preceding first intervals. The operation continues in a repetitive manner under the control of timer 122.

An advantage of this system is that the total flow of blood is independently adjustable by means of blood pump speed control 132. Thus, the amount of blood pumped during each cycle of waveform 130 can be adjusted so that pumping may be slow to start with, and may then be adjusted by means of control 132 for increasing the quantity of blood exchanged to a greater value. The speed of the blood pump during each cycle is determinative of the pressure buildup in the system and the pressure under which the blood is returned to the patient. Also the pump running time and stopping time may be selected by means of adjusting timer 122, independently of the cyclic position of rotor 112, for providing control to keep blood pressure at proper levels. The period of time during which blood is allowed to return to the patient is preferably longer than the pumping period during which blood is withdrawn, as indicated by waveform 130. Notwithstanding the advantages of adjustability regarding the quantity of blood exchanged and blood pressure, the system according to the present invention is quite simple and is reliable in operation.

While we have shown and described a preferred embodiment of our invention, it will be apparent to those skilled in the art that many changes and modifications may be made without departing from our invention in its broader aspects. We therefore intend the appended claims to cover all such changes and modifications as fall within the true spirit and scope of our invention.

We claim:

1. A single passage blood pump system for alternate removal of blood from and return of blood to said single passage, said system comprising:
   a blood flow loop communicating with said passage at ends thereof for withdrawing blood from said single passage and returning blood to said single passage, said loop including a blood pump for producing a flow of blood in said loop,
   a valve means distinct from said pump and positioned in said loop between the outflow side of said blood pump and said single passage,
   blood receiving means also in said blood flow path through which blood is circulated by said blood pump for subsequent return to said single passage, said blood receiving means being positioned between the outflow side of said blood pump and said valve means,
   and timing means coupled in control relation to said blood pump and said valve means and operable independently of the pressure in the system,
   said timing means engaging said valve means on a substantially periodic basis independent of the pressure in the system to prevent the return of blood to said single passage from said blood receiving means and at substantially the same time causing said pump to be energized to pump blood from said single passage toward said blood receiving means, said timing means also disengaging said valve means on a substantially periodic basis independent of the pressure in the system to permit the return of blood to said single passage from said blood receiving means and at substantially the same time causing said pump to be deenergized to prevent the flow of blood from said single passage toward said blood receiving means.

2. The system according to claim 1 wherein said blood receiving means is characterized by expansible properties for retaining the pressure produced by said pump during time periods when said pump is energized to pump blood toward said blood receiving means from said single passage and for releasing the retained pressure during time periods when said pump is deenergized to aid the return of blood to said single passage.

3. The system according to claim 1 wherein said blood pump comprises a roller-and-flexible-tube pump having a tube thereof inserted in said blood flow loop for producing the transfer of liquid along said loop.

4. A single needle alternating flow blood pump system for alternate removal of blood from a blood vessel and return to said blood vessel via a single needle, said system comprising:
   a blood flow path including a blood pump and tubing means communicating between said needle and said blood pump for withdrawing blood from said blood vessel,
   blood receiving means also in said blood flow path through which blood is circulated by said blood pump for subsequent return to said needle,
   solenoid operated valve means in said blood flow path for controllably impeding and opening the passage of blood along said blood flow path,
   and a timer coupled in control relation to said blood pump and operable independently of the pressure in the system for regularly energizing the same to pump blood during first intervals separated by second non-pumping intervals, said timer being further coupled in control relation to said valve means and operable independently of the pressure in the system for regularly operating said valve means in substantial synchronism with said pump to impede the passage of blood along said blood flow path during said first intervals and to open said blood flow path to the passage of blood during said second non-pumping intervals to provide for alternate withdrawal and return of blood via the same needle.

5. The system according to claim 4 wherein said blood receiving means is located on the outflow side of said blood pump and said valve means is located between the outflow side of said blood receiving means and said single needle.

6. The system according to claim 4 wherein said blood pump comprises a roller-and-flexible-tube pump having a tube thereof inserted in said blood flow path for producing the transport of liquid along said path, said pump having a motor which is energized during said first intervals in response to control by said timer, said motor having a speed control which is independent of said timer for governing the speed of operation thereof during said first intervals.

7. A single passage blood pump system for alternate removal of blood from and return of blood to said single passage, said system comprising, a blood flow loop communicating with said passage at ends thereof for withdrawing blood from said single passage and returning blood to said single passage, said loop including a blood pump for producing a flow of blood in said loop, solenoid operated valve means in said blood flow loop between the outflow side of said blood pump and said single passage for controllably impeding and opening the passage of blood along said blood flow loop, said loop also including blood receiving means between said valve means and said blood pump wherein said blood receiving means is characterized by expansible properties, and means independent of the pressure in the system for alternately operating said blood pump and said valve means on a periodic basis and independent of the pressure in the system to impede the passage of blood when said pump is operating to pump blood toward said blood receiving means and to allow the return of blood to said single passage when said pump is not so operating for alternate withdrawal and return of blood to said single passage.

8. The system according to claim 7 wherein said blood pump comprises a roller-and-flexible-tube pump having a tube thereof inserted in said blood flow loop for producing the transfer of liquid along said loop.

* * * * *

UNITED STATES PATENT OFFICE
CERTIFICATE OF CORRECTION

Patent No. 4,063,554    Dated December 20, 1977

Inventor(s) Charles B. Willock et al.

It is certified that error appears in the above-identified patent and that said Letters Patent are hereby corrected as shown below:

Facing page, item [63] "Nov. 6, 1976" should read -- Nov. 6, 1974 --.

Column 1, line 8, "Nov. 6, 1976" should read -- Nov. 6, 1974 --.

Column 5, line 17, "203" should read -- 208 --.

Signed and Sealed this

Fourth Day of April 1978

[SEAL]

Attest:

RUTH C. MASON
Attesting Officer

LUTRELLE F. PARKER
Acting Commissioner of Patents and Trademarks